United States Patent
Oehler et al.

(10) Patent No.: US 10,588,571 B2
(45) Date of Patent: Mar. 17, 2020

(54) SYSTEM, METHOD AND COMPUTER PROGRAM FOR CAPACITIVELY RECORDING ELECTRICAL BIO-SIGNALS

(71) Applicant: CAPICAL GMBH, Braunschweig (DE)

(72) Inventors: Martin Oehler, Braunschweig (DE); Ilya Elenskiy, Braunschweig (DE)

(73) Assignee: CAPICAL GMBH, Braunschweig (DE)

( * ) Notice: Subject to any disclaimer, the term of this patent is extended or adjusted under 35 U.S.C. 154(b) by 39 days.

(21) Appl. No.: 15/745,446

(22) PCT Filed: Jul. 14, 2016

(86) PCT No.: PCT/EP2016/066784
§ 371 (c)(1),
(2) Date: Jan. 17, 2018

(87) PCT Pub. No.: WO2017/012987
PCT Pub. Date: Jan. 26, 2017

(65) Prior Publication Data
US 2018/0206790 A1   Jul. 26, 2018

(30) Foreign Application Priority Data
Jul. 17, 2015   (DE) .................. 10 2015 111 658

(51) Int. Cl.
*G01R 27/26*   (2006.01)
*A61B 5/00*   (2006.01)
(Continued)

(52) U.S. Cl.
CPC .......... *A61B 5/6843* (2013.01); *A61B 5/0245* (2013.01); *A61B 5/6893* (2013.01);
(Continued)

(58) Field of Classification Search
CPC .. G01R 27/2605; G01R 15/16; G01R 31/028; G01R 19/0084; G01R 27/02; G01R 27/26; G01R 29/12; G01R 35/005
(Continued)

(56) References Cited

U.S. PATENT DOCUMENTS

2007/0038257 A1   2/2007   Gray
2012/0116198 A1*   5/2012   Veen .................. A61B 5/04284
600/372
(Continued)

FOREIGN PATENT DOCUMENTS

DE   10 2009 050 755 A1   5/2011
EP   2 101 408 A1   9/2009
(Continued)

OTHER PUBLICATIONS

Serteyn et al., "Motion Artifacts in Capacitive ECG Measurements: Reducing the Combined Effect of DC Voltages and Capacitance Changes Using an Injection Signal", IEEE Transactions on Biomedical Engineering, Aug. 15, 2014, pp. 246-273, vol. 62, No. 1, IEEE Service Center, Piscataway, NJ, USA.
(Continued)

*Primary Examiner* — Raul J Rios Russo
(74) *Attorney, Agent, or Firm* — W&C IP (57) ABSTRACT

System for capacitively recording electrical bio-signals from a bio-signal source, wherein the system has at least one capacitive measuring electrode and at least one electronic evaluation unit which is coupled to the measuring electrode and is intended to evaluate the electrical signals from the measuring electrode, and wherein the system also has means for monitoring the quality of the capacitive coupling between the measuring electrode and the bio-signal source, characterized in that the means for monitoring the quality of the capacitive coupling have, in addition to the measuring
(Continued)

electrode(s), at least two injection electrodes which are electrically separated from one another and are intended to feed injection signals into the at least one measuring electrode via the bio-signal source, wherein the system has signal generators for generating a first injection signal and a second injection signal which differs from the first injection signal, which signals are fed into the measuring electrode by means of the injection electrodes via the bio-signal source, and wherein the system has a determination unit which is set up to determine the quality of the capacitive coupling between the measuring electrode and the bio-signal source on the basis of the signals received via the measuring electrode on the basis of the signal components which are contained therein and stem from the first and second injection signals.

9 Claims, 6 Drawing Sheets

(51) Int. Cl.
  *A61B 5/0245* (2006.01)
  *G01R 31/02* (2006.01)
  *G01R 15/16* (2006.01)
  *G01R 19/00* (2006.01)
  *G01R 27/02* (2006.01)
  *G01R 29/12* (2006.01)
  *G01R 35/00* (2006.01)

(52) U.S. Cl.
  CPC ......... *G01R 15/16* (2013.01); *G01R 19/0084* (2013.01); *G01R 27/02* (2013.01); *G01R 27/26* (2013.01); *G01R 27/2605* (2013.01); *G01R 31/028* (2013.01); *A61B 2562/0214* (2013.01); *G01R 29/12* (2013.01); *G01R 35/005* (2013.01)

(58) Field of Classification Search
  USPC .................. 324/76.11–76.83, 600, 649, 658
  See application file for complete search history.

(56) References Cited

U.S. PATENT DOCUMENTS

| | | | | |
|---|---|---|---|---|
| 2013/0278277 | A1* | 10/2013 | Trattler | H03K 17/955 324/679 |
| 2015/0042312 | A1* | 2/2015 | Kim | G01R 15/16 324/126 |
| 2016/0259085 | A1* | 9/2016 | Wilson | E21B 47/123 |
| 2016/0356911 | A1* | 12/2016 | Wilson | G01N 27/221 |
| 2019/0082990 | A1* | 3/2019 | Poltorak | A61B 5/0476 |

FOREIGN PATENT DOCUMENTS

| | | |
|---|---|---|
| WO | 2006/065765 A2 | 6/2006 |
| WO | 2015/045763 A1 | 4/2015 |

OTHER PUBLICATIONS

Serteyn et al., "ECG reconstruction based on the injection of a multi-frequency signal in capacitive measurement systems", 2014 36th Annual International Conference of the IEEE Engineering in Medicine and Biology Society, Aug. 26, 2014, pp. 1864-1867.

Heuer et al., "Unobtrusive In-Vehicle Biosignal Instrumentation for Advanced Driver Assistance and Active Safety", 2010 IEEE EMBS Conference on Biomedical Engineering & Sciences, Nov. 30, 2010, pp. 252-256.

* cited by examiner

SYSTEM, METHOD AND COMPUTER PROGRAM FOR CAPACITIVELY RECORDING ELECTRICAL BIO-SIGNALS

The invention relates to a system for capacitively capturing electrical biosignals from a biosignal source, wherein the system has at least one capacitive measurement electrode and at least one electronic evaluation unit, coupled to the measurement electrode, for evaluating the electrical signals from the measurement electrode, and wherein the system further has means for monitoring the quality of the capacitive coupling between the measurement electrode and the biosignal source. Further, the invention relates to a method for determining the quality of the coupling between at least one measurement electrode of such a system and a biosignal source, and a computer program having program code means, configured to carry out the method.

In general, the invention relates to the field of capturing electrical biosignals by capacitive capture, i.e. without establishing a galvanic contact with the skin. Here, the biosignal source can be any living being, in particular a human. By way of example, ECG signals, EEG signals and similar signals that are able to be captured electrically can be recorded as biosignals. The biosignals can be evaluated, e.g. for medical diagnostic purposes, or as any other indicator signals which, for example, are evaluated further in vehicle systems.

There already are proposals to equip vehicle seats of automobiles with textile capacitive electrodes in order thus to monitor the fitness to drive of a driver at all times. A proposal for such a textile capacitive electrode emerges from DE 10 2013 108 810 A1.

In the case of such instances of capacitive capture of biosignals, it is important for the evaluation of the captured signals to know how good the signal transfer is from the biosignal source to the measurement electrode. By way of example, what may happen in the case of measurement electrodes installed into the vehicle seat is that the person to be captured is placed inexpediently on the seat or other external factors cause a poor signal transfer. Such a case must be distinguishable from the case where the person, i.e. the biosignal source, does not emit biosignals or only emits low biosignals to the measurement electrode for health reasons.

Therefore, there are already proposals to monitor the quality of the capacitive coupling between the measurement electrode and the biosignal source. The proposal of feeding so-called carrier signals into the biosignal source via certain measurement electrodes and of evaluating said carrier signals via other measurement electrodes together with the actual signals to be captured emerges from WO 2015/075692 A1. This proposal appears relatively complicated for a practical implementation in systems that have many measurement electrodes since a correspondingly large number of carrier signals has to be generated. Moreover, there may be crosstalk between various measurement electrodes if a plurality of measurement electrodes inject a carrier signal at the same time.

The invention is therefore based on the object of specifying a system for capacitively capturing electrical biosignals, in which the quality of the capacitive coupling between the measurement electrode and the biosignal source can be determined with less outlay. Further, an advantageous method for determining the quality of the coupling between at least one measurement electrode of such a system and a biosignal source is intended to be specified, and moreover a computer program having program code means for carrying out the method.

According to claim 1, this object is achieved by a system for capacitively capturing electrical biosignals from a biosignal source, wherein the system has at least one capacitive measurement electrode and at least one electronic evaluation unit, coupled to the measurement electrode, for evaluating the electrical signals from the measurement electrode, and wherein the system further has means for monitoring the quality of the capacitive coupling between the measurement electrode and the biosignal source, wherein the means for monitoring the quality of the capacitive coupling have at least two injection electrodes, electrically separated from one another, for feeding injection signals into the at least one measurement electrode via the biosignal source in addition to the measurement electrode or the measurement electrodes, wherein the system has signal generators for producing a first injection signal and a second injection signal that differs from the first injection signal, said injection signals being fed into the measurement electrode via the biosignal source by means of the injection electrodes, and wherein the system has a determination unit which is configured to determine the quality of the capacitive coupling between the measurement electrode and the biosignal source on the basis of the signals received via the measurement electrode on the basis of the signal components contained therein, which originate from the first and second injection signals. As a result of introducing additional injection electrodes, which are present in addition to the measurement electrode or the measurement electrodes of the system and which accordingly do not serve as measurement electrodes, i.e. do not serve for capturing electrical biosignals, it is possible to provide set feed paths for injection signals which, according to their set function, only need to be provided with the electronic wiring required to this end. In particular, the injection electrodes can be embodied as ground electrodes (capacitively or galvanically coupled to the body) within the meaning of DRL (driven right leg) electrodes, as are known from ECG systems. In this way, the injection electrodes can be embodied as electrodes which, in contrast to the measurement electrodes, are already actively driven by amplifiers in each case. Accordingly, the additional outlay for feeding the injection signals is relatively low. Thus, for example, an injection signal in the form of a sinusoidal signal can be added to the common mode rejection signal supplied in any case by a DRL electrode by means of an adder with little outlay, at least with significantly less outlay than would be necessary in the case of a modification of measurement electrodes.

The system according to the invention is advantageous in that two different injection signals can be fed via the two injection electrodes that are separated from one another, said injection signals in turn being able to be captured by means of the measurement electrode or the measurement electrodes via the biosignal source and being distinguishable from one another. Accordingly, the quality of the capacitive coupling between the measurement electrode and the biosignal source can be determined on the basis of the signals received via the measurement electrode on the basis of the signal components contained therein, said signal components originating from the first and second injection signals. Advantageously, it is always only the at least two injection electrodes with the injection signals that differ from one another that are required, independently of the number of employed measurement electrodes of the system. Hence, it is possible to determine the quality of the capacitive coupling with the biosignal source on the basis of the captured signals for each measurement electrode. To this end, the determination unit may have, for example, a filter for filtering out the signal components originating from the first and second injection signals.

By way of example, a numerical value, for example a numerical value reproducing the coupling capacitance, or else, after an appropriate pre-evaluation, a good/bad information item specifying whether or not the electrical biosignals of the biosignal source captured via a measurement electrode are evaluable in a meaningful manner can be determined as a result of the determination of the quality of the capacitive coupling between the measurement electrode and the biosignal source. In particular, it is also possible to evaluate the temporal profile of the quality of the capacitive coupling determined in this way.

According to an advantageous development of the invention, one, some or all of the measurement electrodes of the system are embodied as textile capacitive electrodes, which are embedded into a textile structure. The textile structure can be, for example, part of an item of seating furniture or a seat in a means of transport, e.g. in a motor vehicle, an airplane or the like. Here, the measurement electrodes can be embedded, in particular, in a backrest of the seat. Furthermore, the electrodes can be integrated into a couch or a bed.

According to an advantageous development of the invention, the at least two injection electrodes are embodied as textile capacitive electrodes, which are embedded in a textile structure. The injection electrodes can be embedded, for example, in a seating area of a seat. As a result, the assumption of relatively good coupling with the biosignal source can be made at all times.

In this way, it is possible to specify a textile structure that is equipped with the measurement electrodes and/or the injection electrodes, it being possible to provide said textile structure in a simple and cost-effective manner. As a result of the embodiment of the electrodes as textile capacitive electrodes, these do not appear to be very bulky and do not interfere with the seating comfort.

According to an advantageous development of the invention, provision is made for one, some or all of the measurement electrodes of the system to be embodied as flexible capacitive electrodes with conductive structures, wherein the conductive structures are embodied as printed structures. Accordingly, the conductive structures can be realized using a printing method. By way of example, the conductive structures can be embodied as screen-printed structures, i.e. they can be realized by means of screen printing. Other printing methods are also advantageously applicable, such as e.g. offset printing, intaglio printing or flexography. As a result of this, it is possible to provide particularly flexibly adaptable capacitive electrodes which, moreover, are producible in large numbers in a cost-effective manner.

According to an advantageous development of the invention, only the first injection signal is fed into the one injection electrode and a superposition of the first injection signal and second injection signal is fed into the other injection electrode. According to an advantageous development of the invention, a common mode rejection signal is additionally fed in both injection electrodes.

According to an advantageous development of the invention, the determination unit is configured to determine the quality of the capacitive coupling on the basis of the amplitude values and phase angles of the signal components of the first injection signal and of the second injection signal received via the measurement electrode.

According to an advantageous development of the invention, the system is configured to determine the heart rate or a variable of the biosignal source derived therefrom.

According to an advantageous development of the invention, measurement values of the currents fed via the first injection electrode and the second injection electrode by means of the supplied injection signals are supplied to the determination unit as further input variables and the determination unit is configured to determine the quality of the capacitive coupling taking into account the supplied measurement values of the currents fed into the first injection electrode and the second injection electrode by means of the supplied injection signals. By way of example, the fed currents can be ascertained by means of shunts. In this way, it is possible to capture further electrical measurement variables for evaluating the variables fed by means of the injection electrodes, and so the computational determination of the quality of the capacitive coupling of the measurement electrode is further simplified.

The object set forth at the outset is further achieved by a method for determining the quality of the coupling between at least one measurement electrode of a system of the type described above and a biosignal source, including the steps of:

a) feeding, with temporal overlap or at the same time, a first injection signal and a second injection signal, differing therefrom, into the at least one measurement electrode via the biosignal source, b) evaluating the electrical signals received by the at least one measurement electrode, c) determining the quality of the capacitive coupling on the basis of the signal components of the first injection signal and of the second injection signal contained in the received signals.

The advantages explained above can also be realized hereby.

The object set forth at the outset is moreover achieved by a computer program having program code means, configured to carry out the method of the type described above when the computer program is executed on a computer of the system. By way of example, the computer of the system can be a computer of the determination unit. The advantages explained above are also realized hereby.

The invention will be explained in more detail below on the basis of exemplary embodiments, with drawings being used in the process.

In the figures.

The same reference signs for mutually corresponding elements are used in the figures.

Figure 1:
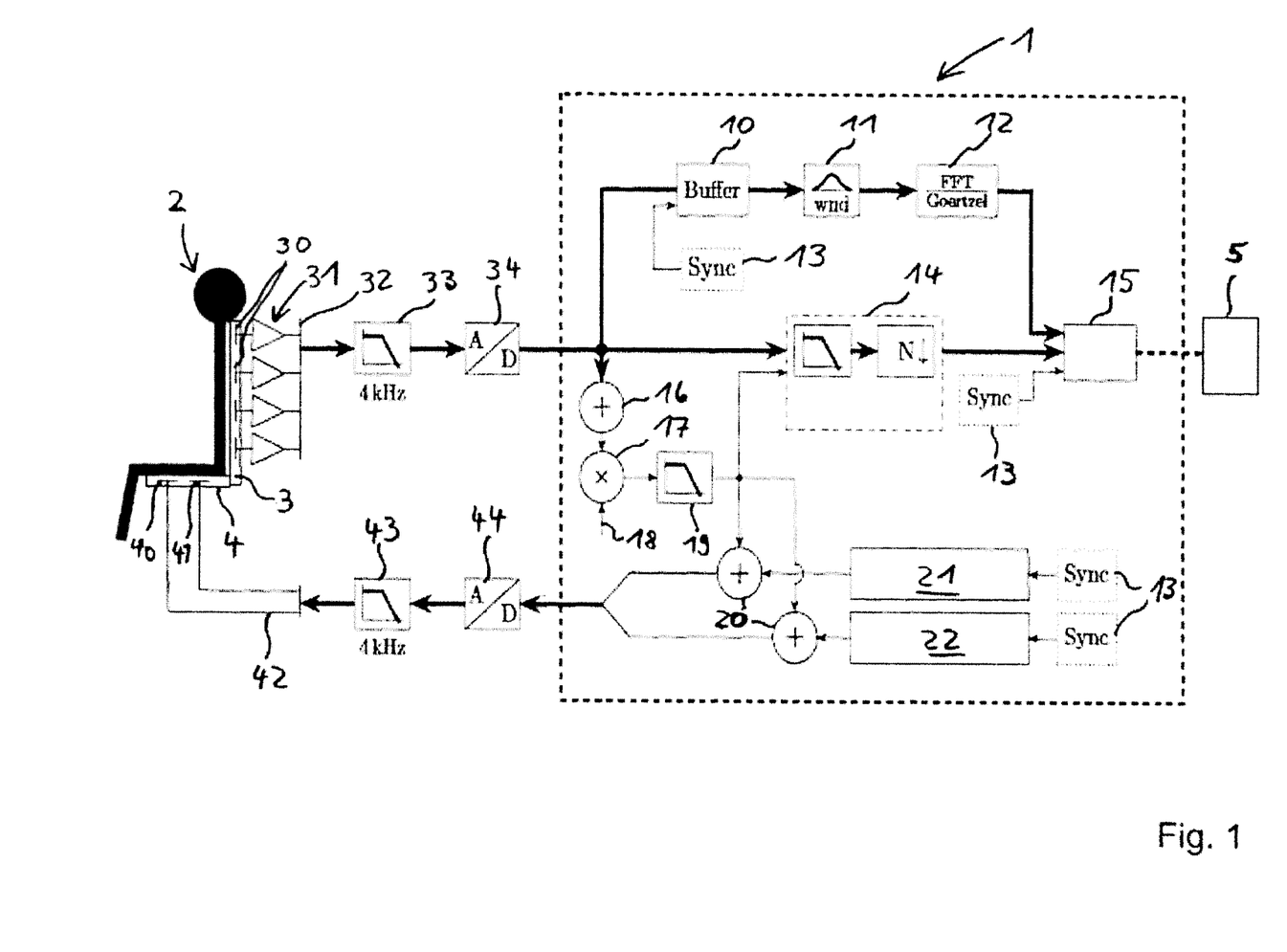
FIG. 1 shows a system according to the invention in a schematic illustration and FIG. 2 shows the multi-layer structure of a textile electrode and FIG. 3 shows a signal capturing circuit of a measurement electrode and FIG. 4 shows an equivalent circuit diagram of a 2-channel system and FIG. 5 shows an equivalent circuit diagram of the injection electrodes and FIG. 6 shows a schematic of an alternative seat used in the system shown in FIG. 1.
Figure 6:
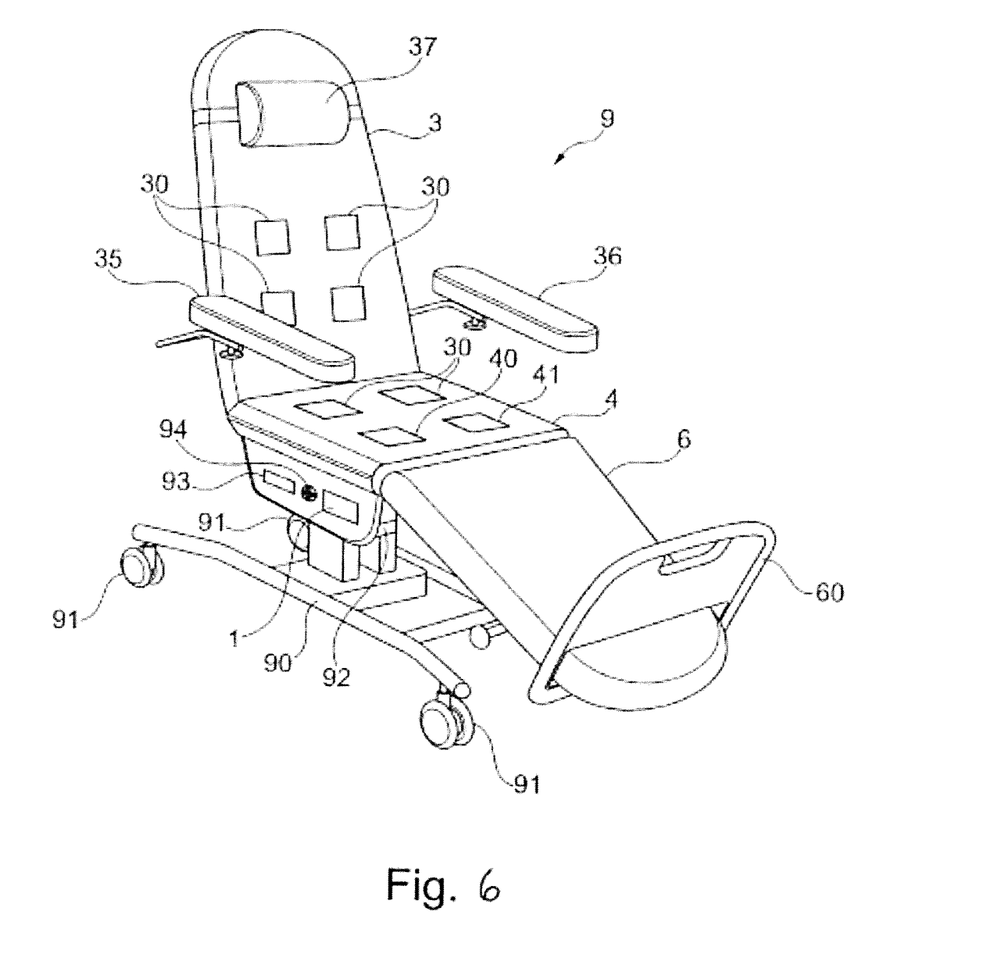

The system illustrated in FIG. 1 serves for capacitively capturing electrical biosignals from a biosignal source 2, e.g. a human. To this end, a seat upholstered with textiles, e.g. a vehicle seat, is equipped with appropriate capacitive measurement electrodes and injection electrodes (see also FIG. 6). Presented in an exemplary manner is that four measurement electrodes 30 in the form of textile capacitive electrodes are integrated into a backrest 3 of the seat. Two injection electrodes 40, 41 are integrated into a seating area 4 of the seat, it likewise being possible for said injection electrodes to be embodied as textile capacitive electrodes. The injection electrodes 40, 41 are connected by separate electrical lines with devices 43, 44, which have only been illustrated once in FIG. 1 but which are realized separately for each injection electrode. The device 43 is a low-pass filter, for example with a limit frequency of 4 kHz. The device 44 is embodied as a digital-to-analog transducer, which converts a digital signal supplied from a determination unit 1 into an analog voltage value and which outputs said analog voltage value to the respective injection electrode 40, 41 via the low-pass filter 43.

The measurement electrodes 30 are connected to further signal processing means 33, 34 via respective signal amplifiers 31, which may also be integrated in the respective textile electrode. The measurement electrodes 30, or their signal amplifiers 31, can be connected to the determination unit 1 in each case via an individual, separate signal path via signal processing means 33, 34 or, if the circuitry outlay should be reduced, they can be connected to the same signal processing means 33, 34 via a multiplexer 32 in each case. The signal processing means 33 can be embodied as a low-pass filter, for example with a limit frequency of 4 kHz. The signal processing means 34 can be embodied as an analog-to-digital transducer.

By means of the respective analog-to-digital conversion and digital-to-analog conversion, it is possible for the signal processing in the determination unit 1 to be effectuated in a completely digital manner, with the advantage that it is possible to realize complex signal processing algorithms relatively cheaply.

The determination unit 1 connected to the analog-to-digital transducer 34 and the digital-to-analog transducers 44 has the following structure: the digitized signals from the measurement electrode 30, captured via the analog-to-digital converter 34, are supplied to three different evaluation paths in the determination unit 1, to be precise to a path for evaluating the signal components originating from the injection signals, a path for ascertaining the actual used signals, namely the biosignals from the biosignal source, and a path which serves for common mode rejection. The discussion will initially focus on the path for evaluating the signal components originating from the injection signals. To this end, a buffer 10 is initially present, the incoming data initially being buffered once therein block-by-block, for example with a block size of 728 measurement values. Here, in particular, the block size is selected in such a way that full periods of the first injection signal and the second injection signal are stored in a block in each case.

The signal components are pre-processed in a block 11 using a non-rectangular window function, for example a Hanning window. There is further filtering in a subsequent digital filter 12, for example by means of a Fast Fourier Transform (FFT) or a Goertzel algorithm. The Goertzel algorithm allows the efficient determination of selected frequency components. Using the data determined in this manner, the quality of the capacitive coupling between the measurement electrode and the biosignal source can be determined, for example in the form of the coupling capacitance, in a block 15. The results of the quality determination can be output, for example, on a display device, e.g. a monitor 5, or may be supplied to further processing.

The ECG signals are filtered out of the supplied signals from the measurement electrode via the filter block 14 illustrated approximately in the center of the determination unit 1 in FIG. 1. By way of example, this can be effectuated by way of a low-pass filter.

For the common mode rejection, provision is made for initially summing the supplied, digitized measurement signal via a summing unit 16. As a result of this, the common mode signal is obtained. The previously determined common mode signal still can be amplified by an amplification factor 18, for example in the range from 0 to 40 dB, in a multiplying unit 17. The signal formed thereby is subsequently supplied to a further filter 19. The signal produced by the filter 19 is supplied, firstly, to the filter block 14 and, moreover, to two summing units 20.

The first injection signal and the second injection signal are produced in two signal generators 21, 22 in the blocks illustrated at the bottom of the determination unit 1. By way of example, the first injection signal can have a frequency of 1120 Hz at 100 mV amplitude while the second injection signal can have a frequency of 1040 Hz at 12.5 mV amplitude. Thus, the first signal generator 21 may be embodied to directly emit a superposition of the first injection signal and the second injection signal, while the other signal generator 22 only emits the first injection signal. The signal output by the filter 19 is mixed into the respective injection signals in the summing units 20 for the purposes of common mode rejection. The corresponding signals, which are present in digital form up to this point, are converted into analog signals via the aforementioned digital-to-analog transducers 44 and fed into the injection electrodes 40, 41 separately from one another via the filters 43.

A compromise was found for the dimensioning of the injection signals, said compromise allowing the placement of the injection signals at frequencies that lie together as closely as possible and the offering of a good demodulation rate and, in the process, allowing achievable sensing rates for suitable precision analog-to-digital transducers and available microcontrollers. Moreover, the injection frequencies must be high enough to be able to be sufficiently suppressed in relation to the used signal (the ECG signal) using a simple low-pass filter. As a result of this, a delimitation from movement artifacts, which lie in the range below 20 Hz, is also possible.

The amplitude of the injection signals also represents a compromise between a good signal-to-noise ratio and the lowest possible order of the low-pass filters to facilitate simple signal processing.

Figure 2:
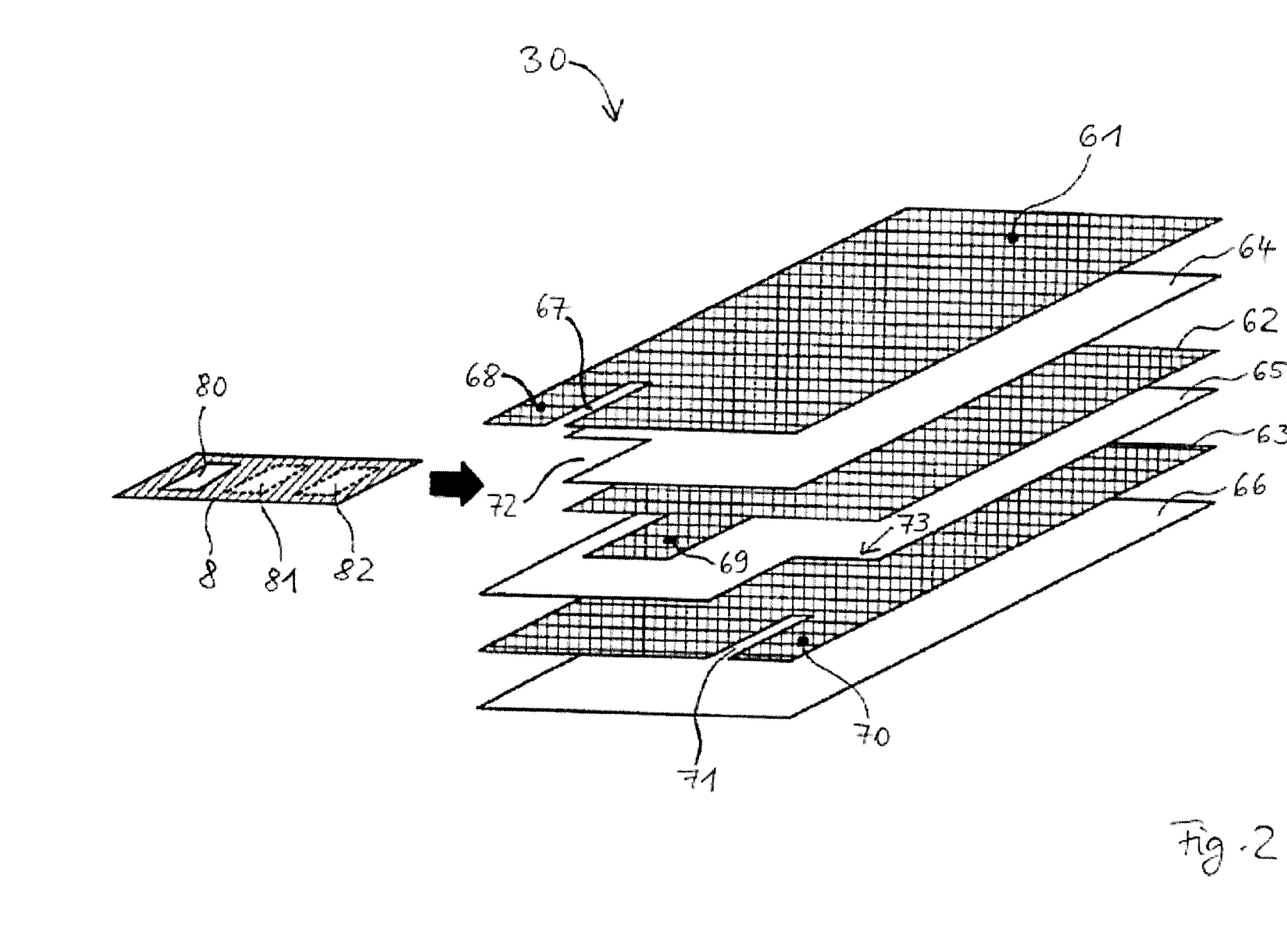

FIG. 2 shows, in an exemplary manner, a textile electrode as can be used as measurement electrode 30 or else as injection electrode 40, 41. At this point, reference is once again made to the fact that the invention is not restricted to textile electrodes but, instead, is usable with any type of capacitive electrode.

FIG. 2 shows the electrode 1 with the individual layers in an isometric view, before the layers are adhesively bonded together. It is possible to identify three electrically conductive layers 61, 62, 63 made of an electrically conductive textile material and three insulation layers 64, 65, 66 made of an insulating textile material. The uppermost electrically conductive layer 61 is the sensor layer of the electrode which serves for capacitively coupling the signal to be measured by means of the electrode. The electrically conductive layer 62 in the middle is a guard layer which serves to shield the sensor layer 61 from external disturbing influences, in particular ESD influences. The lowermost electrically conductive layer 63 is a reference potential layer which should be connected to a reference potential. In one corner, the sensor layer 61 has a recess 67, by means of which a contact tab 68 is formed for electrically contacting the sensor layer 61. The guard layer 62 has a contact tab 69, which is formed by virtue of pieces of textile material of the guard layer 62 having been cut away to the left and to the right of the contact tab 69. The contact tab 69 serves for electrical contacting of the guard layer 62. The reference potential layer 63 has a comparable embodiment to the sensor layer 61; however, it has a contact tab 70 on the opposite side. The contact tab 70 is formed as a consequence of a recess 71, which is cut out of the textile material of the reference potential layer 63. The uppermost insulation layer 64 has a recess 72 in one corner, said recess lying below the contact tab 68. The insulation layer 65 in the middle has a recess 73 in an opposite corner of the same side. The recess 73 overlaps with the contact tab 70. The lowermost insulation layer 66 does not have any such recess. By way of example, the layers 61-66 can be brought into the described and illustrated outer contour by laser cutting.

The outer form of the electrode 1 or of the individual layers 61-66 need not necessarily be substantially rectangular, as illustrated in FIG. 2, but can instead assume any other desired form, such as e.g. an oval form, a rectangular form with rounded corners or a circular form.

Amplifier electronics 83 which serve to amplify the electrical signals output by the capacitive electrode 1 are integrated into the region in which the contact tabs 68, 69, 70 are present in the multilayer structure illustrated in FIG. 2. The amplifier electronics 83 are arranged between the upper insulation layer 64 and the guard layer 62 in this case. However, this is only one example for a possible arrangement; advantageously, other positions of the amplifier electronics 83 are also possible. The amplifier electronics 83 have an electrical connection surface 80 on the side that is illustrated at the top in FIG. 2 and two further electrical connection surfaces 81, 82, for example in the form of contact pads, on the lower side. As a consequence of the recesses 72, 73, the contact tab 68 can be electrically connected to the connection surface 80, the contact tab 69 can be electrically connected to the connection surface 81 and the contact tab 70 can be electrically connected to the connection surface 82. As a consequence of the insulation layers 64, 65, 66 that overlap in the remaining regions, there cannot be unwanted short circuits or faulty contacting.

Figure 3:
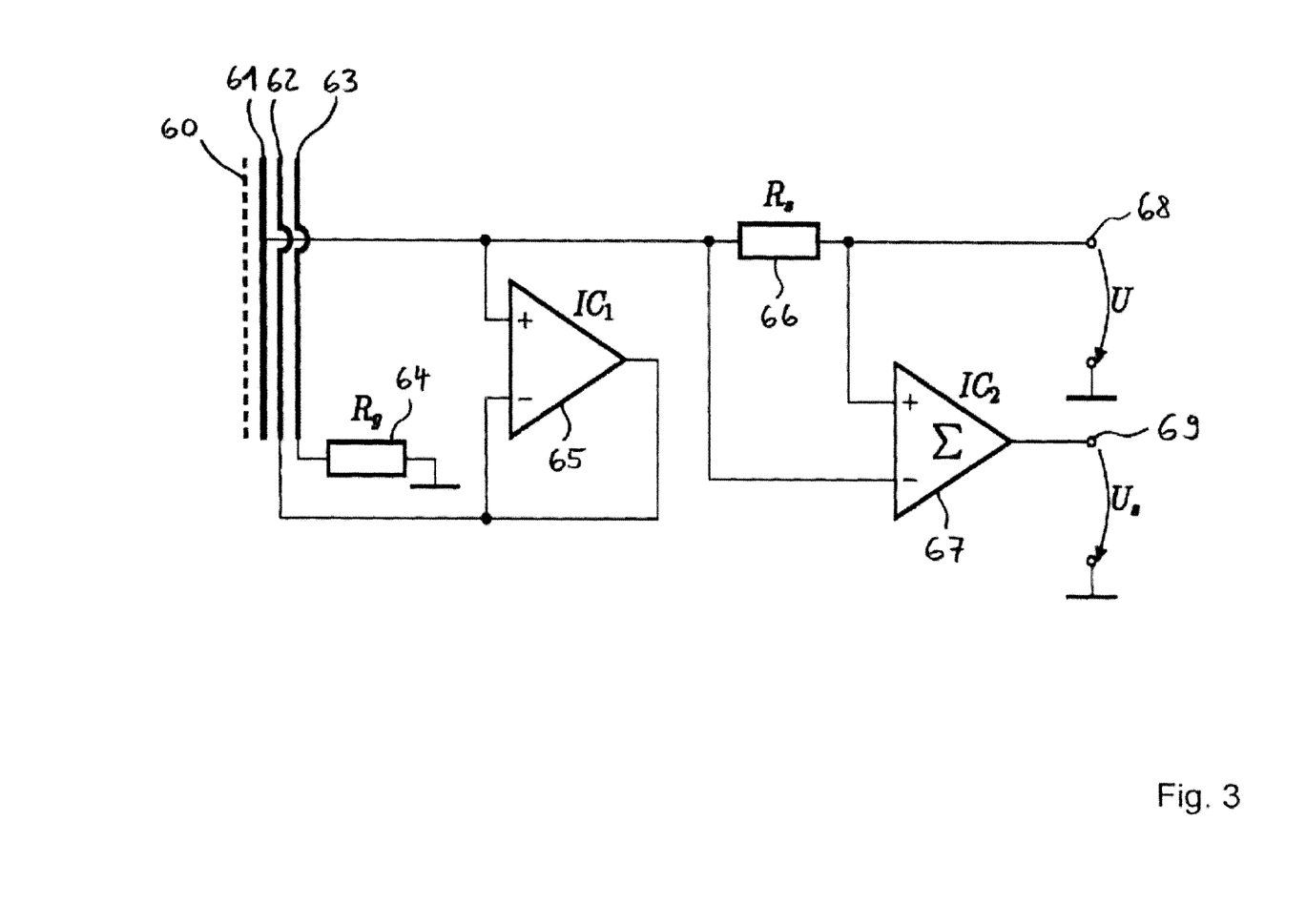

FIG. 3 shows, in an exemplary manner, a ground electrode with the above-described multilayer structure to the left, said multilayer structure being arranged behind the textile surface 60 of the backrest 3. The reference potential layer 63 is connected to the system ground via a resistor 64. The sensor layer 61 is connected via a line, initially via an amplifier, e.g. an operational amplifier 65, to the guard layer 62. Further, for the purposes of capturing the already explained signals that are to be captured by way of the measurement electrode, the sensor layer 61 is connected to a measurement connector 68, at which the measurement signal to be captured by means of the signal evaluation means 33, 34 is present. In order to be additionally able to carry out a current measurement in respect of the injection electrodes 40, 41, a measurement resistor in the form of a shunt 66 is present in the line from the sensor layer 61 to the measurement connector 68. The voltage drop across the shunt 66, which is an indicator for the current flowing therethrough, is amplified via an amplifier 67 and output to an output connector 69. The signal provided at the output connector 69 is supplied, likewise via an analog-to-digital converter, to the determination unit 1, optionally after preceding filtering, and processed further there.

The quality of the capacitive coupling, for example in the form of a coupling impedance, can be determined as outlined below: here, the equivalent circuit diagram illustrated in FIG. 4 and the electrical variables specified therein are taken as a starting point.

Figure 4:
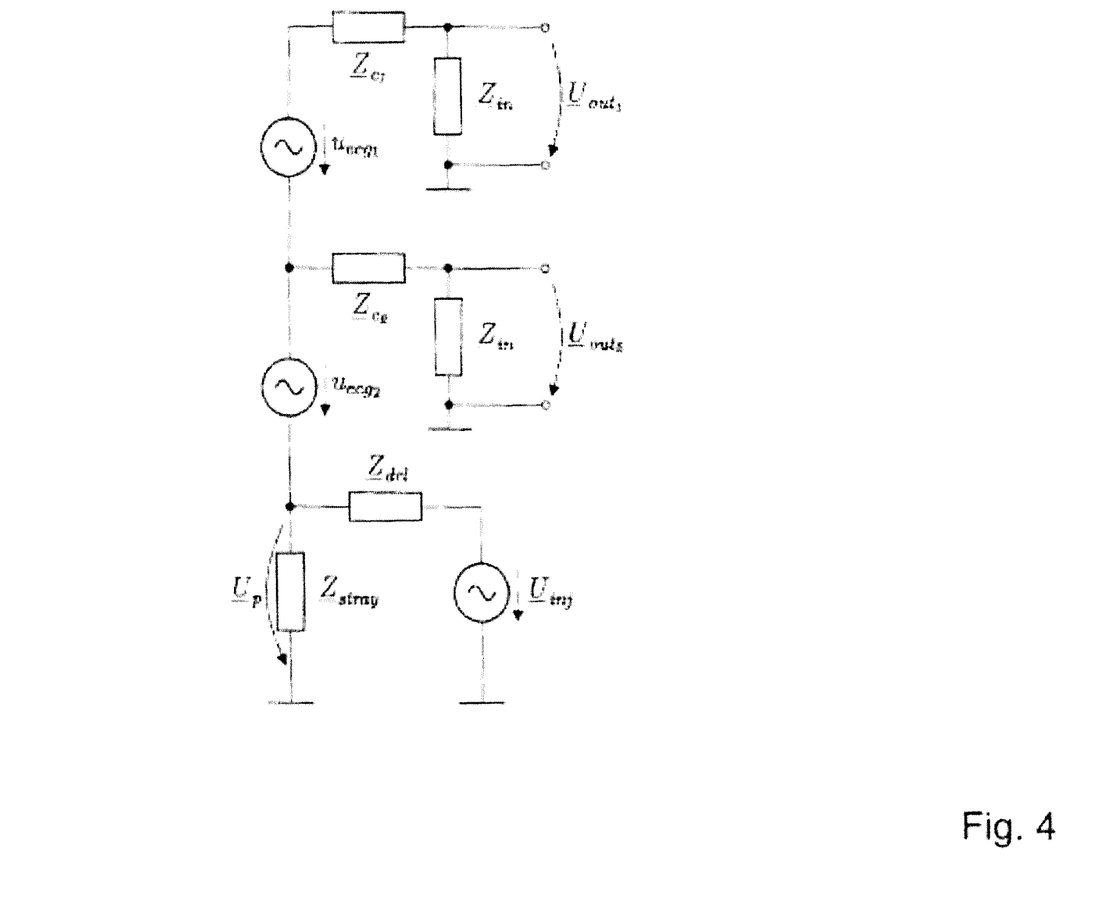

FIG. 4 illustrates the equivalent circuit diagram of a 2-channel system (two measurement electrodes) with a DRL signal injection. Additionally, the parasitic impedance $Z_{stray}$ is taken into account here. It arises from the stray capacitances between the biosignal source and objects in the environment and between the measurement system and the environment. It is particularly significant in the case of a non-insulated power supply of the measurement system from the grid. $U_p$ represents the voltage signal present at the biosignal source in relation to the system ground. The following applies for the coupling impedance of an electrode:

$$\underline{U}_{out} = \underline{U}_p \frac{Z_{in}}{Z_{in} + Z_c} \quad (3.11)$$

$$\Leftrightarrow Z_c = Z_{in}\left(\frac{U_p}{U_{out}} - 1\right) \quad (3.12)$$

From this, it is possible to determine the capacitance and the resistance depending on the angular frequency ω of the injection signal:

$$C_c = \frac{\mathcal{I}(\underline{Y}_c)}{\omega} = \frac{\mathcal{I}\left(\frac{1}{Z_c}\right)}{\omega} \quad (3.13)$$

$$R_c = \frac{1}{\mathcal{R}(\underline{Y}_c)} = \frac{1}{\mathcal{R}\left(\frac{1}{Z_c}\right)} \quad (3.14)$$

$$(3.15)$$

However, the model shows that the voltage $U_p$ is influenced by the impedances $Z_{stray}$, $Z_{drl}$ and $Z_{ci}$. It cannot be uniquely determined with the available measurement data.

In order to be able to determine $U_p$, at least one further injecting electrode is required.

To this end, the DRL electrode can be subdivided into two separate areas in order to form the injection electrodes. In contrast to the subdivision of the measurement electrodes, this does not harbor a disadvantage for the signal quality since only the overall capacitance of the two areas has to be maximized in the case of the DRL electrode. The corresponding equivalent circuit diagram can be seen in FIG. 5; here, the electrode and stray capacitances are combined to the impedance $Z_p$. Two injection signals are fed: $U_{inj2}$ with the angular frequency $\omega_2$ over both areas and $U_{inj1}$ with the angular frequency $\omega_1$ over the first area only. The two parts of the electrode each contain a shunt $Z_{s1}$ and $Z_{s2}$, respectively. By measuring the voltage of the shunts, it is possible to determine the complex currents $I_{s1}$ and $I_{s2}$ for the two angular frequencies $\omega_1$ and $\omega_2$. The shunts should be selected to be resistive: as the injection signals lie above the ECG bandwidth, the predominantly capacitive coupling impedances $Z_{drli}$, $\omega_i$ are smaller in relation to the injection signal than in relation to the ECG signal. However, the resistive impedances of the shunts remain unchanged. Consequently, these only produce a small voltage drop in the frequency band of the ECG signal and consequently do not reduce the effectiveness of the DRL electrode, whereas the voltage drop in the band of the injection signals becomes larger and consequently allows a more precise determination of $I_s$. Moreover, the model has the input impedances $Z_{in1}$ and $Z_{in2}$, which model the corresponding parasitic properties of the amplifiers used for the shunt voltage measurement.

Figure 5:
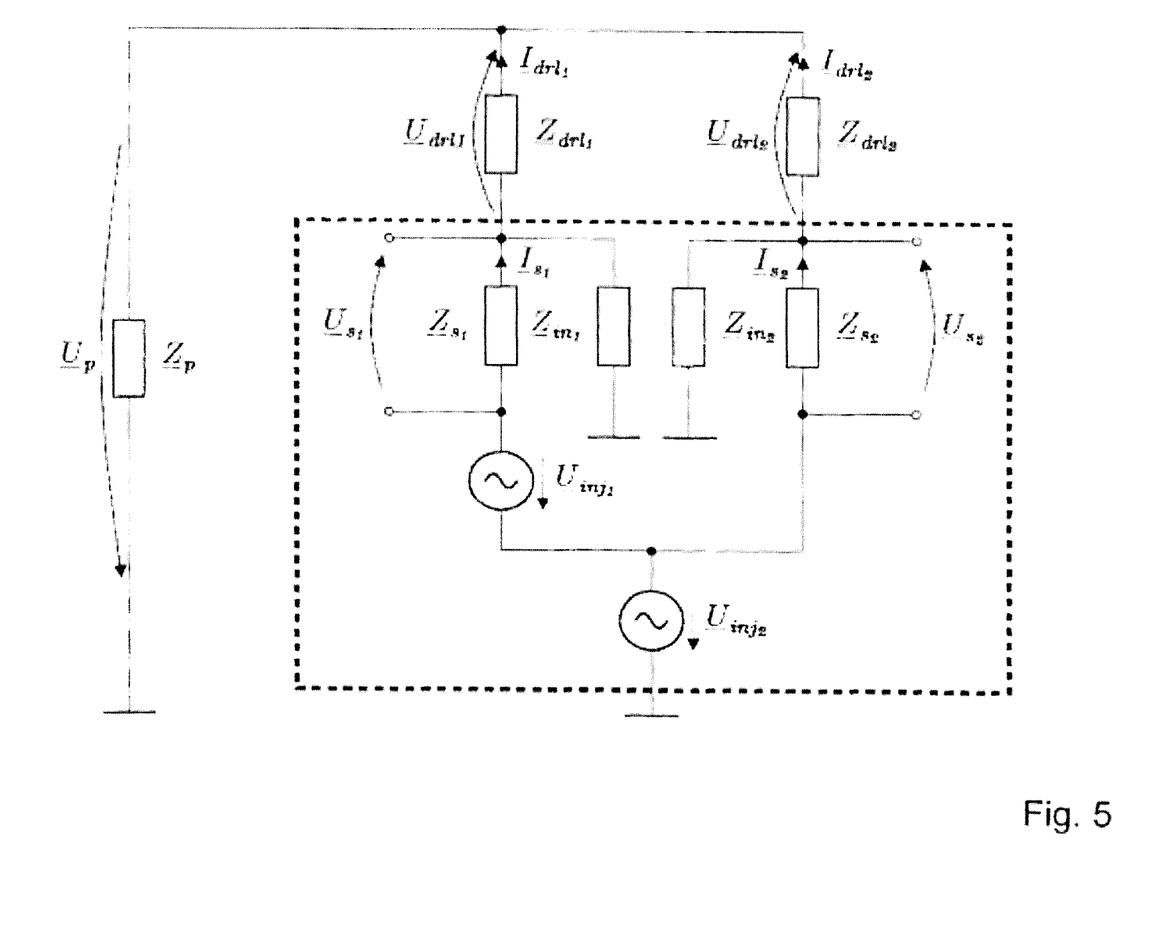

It should now be shown that the voltage $U_p$, $\omega_2$ present at the patient and the two coupling capacitances $Z_{drl1}$, $\omega_2$, $Z_{drl2}$, $\omega_2$ of the DRL electrode can be determined using the voltages $U_{s1}$, $\omega_2$ and $U_{s2}$, $\omega_1$ and $U_{s1}$, $\omega_2$ and $U_{s2}$, $\omega_2$ measured at the shunts. The method with the aid of which the frequency components $\omega_1$ and $\omega_2$ belonging to the respective injection signals $U_{inj1}$ and $U_{inj2}$ can be demodulated from the measurement signal was already described above. When determining the voltages and the currents with the index $\omega_1$, the voltage source $U_{inj2}$ is assumed as a short circuit, with the index $\omega_2$–$U_{inj1}$. For simplification purposes, the corresponding admittances can be used below instead of the impedances. Initially, the complex currents should be determined by way of the coupling impedances. Kirchhoff's first law shows:

$$I_{drl_1,\omega_i} = Y_{s_1,\omega_i} U_{s_1,\omega_i} - (U_{inj_i} - U_{s_1,\omega_i}) Y_{in_1,\omega_i} \text{ for } i=1,2 \quad (3.16)$$

$$I_{drl_1,\omega_1} = U_{s_2,\omega_1}(Y_{in_2,\omega_1} + Y_{s_2,\omega_1}) \quad (3.17)$$

$$I_{drl_2,\omega_2} = Y_{s_2,\omega_2} U_{s_2,\omega_2} - (U_{inj_2} - U_{s_2,\omega_2}) Y_{in_2,\omega_2} \quad (3.18)$$

In order to simplify the further calculations, two assumptions are made at this point:

The two shunts have such a low resistance in comparison with the coupling impedances that $U_{inj} \gg U_s$ applies for both electrodes and frequencies. From here on, $U_s$ is neglected.

The angular frequencies $\omega_1$ and $\omega_2$ lie so closely together that $Y_{\omega 1} = Y_{\omega 2}$ applies for all admittances. From here on, it is assumed that the admittances are frequency independent.

Kirchhoff's second law shows:

$$0 = \underline{U}_{drl_2,\omega_2} - \underline{U}_{drl_1,\omega_2} = \frac{I_{drl_2,\omega_2}}{Y_{drl_2}} - \frac{I_{drl_1,\omega_2}}{Y_{drl_1}} \quad (3.19)$$

$$\Leftrightarrow \underline{Y}_{drl_2} = \underline{Y}_{drl_1} \frac{I_{drl_2,\omega_2}}{I_{drl}} \quad (3.20)$$

$$0 = -\underline{U}_{inj_1} + \underline{U}_{drl_1,\omega_1} - \underline{U}_{drl_2,\omega_1} = \underline{U}_{inj_1} + \frac{I_{drl_1,\omega_1}}{Y_{drl_1}} - \frac{I_{drl_2,\omega_1}}{Y_{drl_2}} \quad (3.21)$$

Inserting 3.20 into 3.21 and rearranging shows:

$$\underline{Y}_{drl_1} = \frac{1}{\underline{U}_{inj_1}} \left( I_{drl_1,\omega_1} - \frac{I_{drl_2,\omega_1} I_{drl_1,\omega_2}}{I_{drl_2,\omega_2}} \right) \quad (3.22)$$

The following applies for the voltage $U_p$:

$$\underline{U}_{p,\omega_2} = \underline{U}_{inj_2} - \frac{I_{drl_1,\omega_2}}{Y_{drl_1}} = \frac{I_{drl_2,\omega_2}}{Y_{drl_2}} \quad (3.23)$$

Hence, the two coupling impedances of the DRL electrode can be determined from 3.22 and 3.20 and the component of the injection signal present at the biosignal source can be determined from 3.23.

The invention claimed is:

1. A system for capacitively capturing electrical biosignals from a biosignal source, comprising:
   at least one capacitive measurement electrode;
   at least one electronic evaluation unit coupled to the at least one capacitive measurement electrode for evaluating electrical signals from the at least one capacitive measurement electrode; and
   means for monitoring quality of a capacitive coupling between the at least one capacitive measurement electrode and the biosignal source, wherein the means for monitoring the quality of the capacitive coupling has
      at least two injection electrodes which are electrically separated from one another for feeding injection signals into the at least one capacitive measurement electrode via the biosignal source;
      signal generators for producing a first injection signal and a second injection signal that differs from the first injection signal, said first and second injection signals being fed into the at least one capacitive measurement electrode via the biosignal source by means of the at least two injection electrodes; and
      a determination unit comprising a computer which is configured to determine the quality of the capacitive coupling between the at least one capacitive measurement electrode and the biosignal source on the basis of signal components contained in the first and second injection signals received via the at least one capacitive measurement electrode.

2. The system as claimed in claim 1, wherein one or more of the at least one capacitive measurement electrode is or are embodied as textile capacitive electrodes embedded in a textile structure.

3. The system as claimed in claim 1, wherein one or more of the at least one capacitive measurement electrode is or are embodied as flexible capacitive electrodes with conductive structures, wherein the conductive structures are embodied as printed structures.

4. The system as claimed in claim 1 wherein only the first injection signal is fed into one injection electrode of the at least two injection electrodes and a superposition of the first injection signal and second injection signal is fed into a second injection electrode of the at least two injection electrodes.

5. The system as claimed in claim 1 wherein the determination unit is configured to determine the quality of the capacitive coupling on the basis of amplitude values and phase angles of the signal components of the first injection signal and of the second injection signal received via the at least one capacitive measurement electrode.

6. The system as claimed in claim 1 wherein the system is configured to determine heart rate or a variable of the heart rate from the biosignal source.

7. The system as claimed in claim 1 wherein measurement values of currents fed via a first injection electrode and a second injection electrode of the at least two injection electrodes are supplied to the determination unit as input variables, and wherein the determination unit is configured to determine the quality of the capacitive coupling taking into account the measurement values of the currents fed into the first injection electrode and the second injection electrode by means of the first and second injection signals.

8. A method for determining the quality of the coupling between at least one measurement electrode of a system as claimed in claim 1 and a biosignal source, comprising the steps of:
  a) feeding, with temporal overlap or simultaneously, the first injection signal and the second injection signal into the at least one capacitive measurement electrode via the biosignal source,
  b) evaluating the first and second injection signals received by the at least one capacitive measurement electrode, and
  c) determining the quality of the capacitive coupling on the basis of the signal components of the first injection signal and of the second injection signal received by the at least one capacitive measurement electrode.

9. A non-transitory storage medium encoded with a computer program configured to carry out the method as claimed in claim 8, wherein the computer program is executable on the computer of the system.

\* \* \* \* \*